Figure 1:
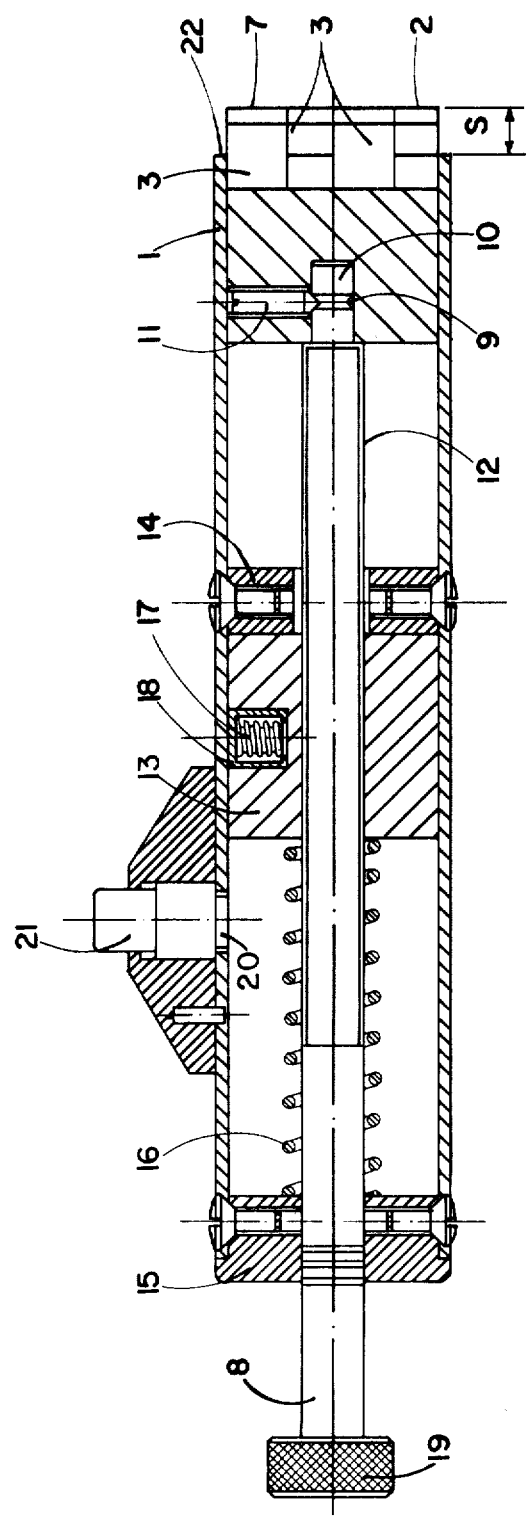

United States Patent [19]

Birchmeier

[11] 4,417,580
[45] Nov. 29, 1983

[54] TISSUE PERFORATOR

[76] Inventor: Alfons Birchmeier, Zürcherstrasse 8, CH-8952 Schlieren, Switzerland

[21] Appl. No.: 220,168

[22] Filed: Dec. 23, 1980

[30] Foreign Application Priority Data

Dec. 21, 1979 [CH] Switzerland ............ 11370/79

[51] Int. Cl.³ .................................. A61B 17/32
[52] U.S. Cl. ............................. 128/315; 128/305; 30/304
[58] Field of Search ............ 128/329 R, 253, 315, 128/355, 305.5, 305; 30/287, 304, 305

[56] References Cited

U.S. PATENT DOCUMENTS

| 5,111 | 5/1847 | Leypoldt | 128/315 |
| 1,672,045 | 6/1928 | Sweeney | 30/305 |
| 3,208,452 | 9/1965 | Stern | 128/329 R X |
| 3,613,242 | 10/1971 | Hill et al. | 128/305.5 X |
| 4,243,038 | 1/1981 | Harnick | 30/305 X |

FOREIGN PATENT DOCUMENTS 1102799 10/1955 France ............ 128/329 R

Primary Examiner—Michael H. Thaler
Attorney, Agent, or Firm—Ernest F. Marmorek

[57] ABSTRACT

In order to remove as much poison as possible from bites or stings of poisonous animals, a plurality of incisions is made into the flesh tissue being at least approximately parallel to each other and several times interrupted in their longitudinal direction. For this a tissue perforating device is used, which is equipped with a knive head (2) abruptly movable in the interior of a housing member (1). The knive head being provided with three rows of knives offset lateral, the cutting edge (7) of the knives being rectilinear and at right angles to the direction of penetration into the tissue.

2 Claims, 6 Drawing Figures

TISSUE PERFORATOR

The invention relates to a tissue perforating device and to a process for treating bites or stings of poisonous animals.

In times of old, one hardly knew how to treat persons bitten or stung by poisonous animals. As a rule they died under great pain shortly after the bite or sting, respectively, or later by the necrosis caused by an infection of the affected part of the body.

In later times one tried to remove as much poison as possible from the wound or to neutralise it by cutting, sucking off, burning out or rubbing-in crystals of potassium permangate. None of these methods, however, achieved the desired success.

Today one generally uses a serum in the case of such injuries but this method has the disadvantage that the serum is relatively expensive and can be preserved only for a limited time.

It is a task of the present invention to provide a device which does not show the above mentioned disadvantages of the methods known up to date and allows a simple and safe treatment of injures caused by bites or stings or poisonous animals.

This task is achieved according to the invention by a tissue perforating device which is characterized in that it is equipped with a knife head being provided with at least two knives arranged side by side and with knives offset in relation to them, all the knives being approximately parallel to each other and their cutting edge being at least approximately rectilinear and at least approximately at right angles to the direction of penetration into the tissue.

It is suitable that the knife head is shiftably guided inside a holding member, that a tensioning arrangement is provided for tensioning the knife head against the action of a tensioning spring and to keep it in the tensioned condition, and that the device is also equipped with a release arrangement for releasing the tensioned knife head so that it is abruptly moved in the percussion direction under the action of the tensioning spring.

In order to provide a device that is equally well suitable for treating injuries on large-area body portions, for instance on the thigh, and on small-area body portions, for instance on fingers, it has been found to be of advantage if the knife head is provided with six knives arranged in three rows.

Moreover, it is of advantage if the length of the knives is 3 to 5 mm, preferably about 4 mm, if the distance of the two neighbouring rows of knives corresponds to one half of the knife length, and if the knives of two neighbouring rows of knives are offset by one half to one knife length. It is also suitable if the height of the knives is 3 to 7 mm, preferably about 5 mm.

Furthermore, it is suitable if the knives are sharpened on both sides for forming the rectilinear cutting edge.

In addition, it is of advantage if there is provided a spindle rotatable in relation to the knife head and longitudinally extending in the shifting direction of said knife head beyond the holding member, if the spindle is in engagement by its thread with a path limiting member which is movable in relation to the holding member in the shifting direction of the knife head but guided so as to be non-rotatable, and if the holding member is provided with a stop which limits the movement of the path limiting member in the direction of percussion.

It is further of advantage if the spindle, the path limiting member and the stop are so arranged and shaped that when the path limiting member is applied to the stop, it is possible by turning the spindle to withdraw the knife head with the aid of said spindle so far into the holding member that the knives are inside the holding members. It is also of advantage if the path limiting member is provided with a lock member or catch which, in the tensioned condition of the device, engages a part of the holding member.

A further object of the present invention is a process for treating injuries by bites or stings of poisonous animals, characterised in that preferably after applying a ligature between such an injury and the heart, one produces preferably by a device according to the invention a plurality of incisions into the flesh tissue being at least approximately parallel to each other and several times interrupted in their longitudinal direction, and that subsequently poison-containing tissue liquor is sucked off from these incisions by means of underpressure.

It is suitable if the underpressure is produced by means of a suction bell which can be applied to the flesh tissue in the range of the injury so as to seal said tissue from the surroundings, said suction bell being connected by a suction channel with a cylinder and piston unit, a compression spring being arranged in the interior of the cylinder of said unit, which compression spring acts on the piston and presses it outwards.

Figure 4A:
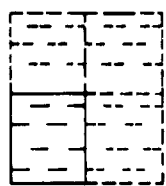
Figure 4B:
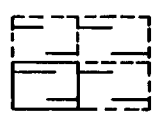
Figure 5:
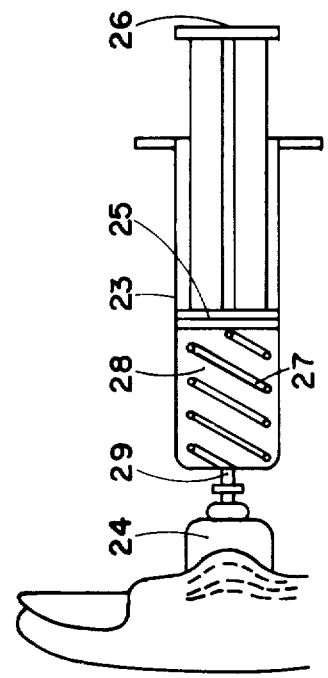
Figure 2:
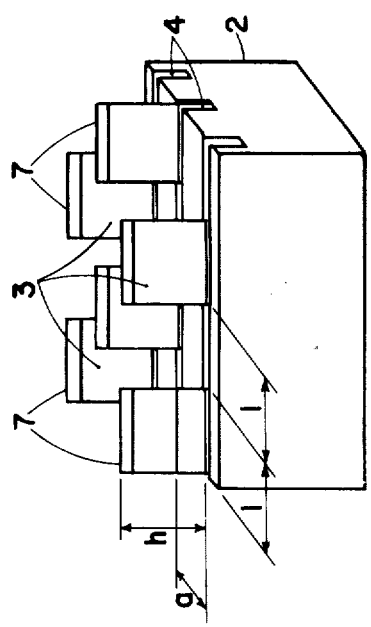
Figure 3:
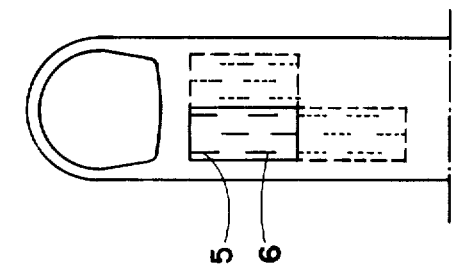

The invention will now be explained by way of example with reference to the accompanying drawings, in which shows:

FIG. 1 a longitudinal section through an example of an embodiment of a tissue perforating device according to the invention;

FIG. 2 on a larger scale a perspective view of the knife head used in the device shown in FIG. 1;

FIG. 3 the perforation pattern produced by the device shown in FIGS. 1 and 2;

FIGS. 4a and 4b by way of example further possible arrangements of the knives; and FIG. 5 by way of example an application of the device according to the invention.

As can be seen in FIG. 1, the tissue perforating device is shown equipped with a housing and holding member 1 of rectangular cross section and employed as a guide member.

The knife head 2 is shiftably guided in the interior of the guide member 1. As can be seen especially in FIG. 2, the knife head 2 is provided with six knives 3 which are fixed by guiding them parallel to each other into three grooves 4 arranged side by side. In order to avoid tearing of the swollen tissue present between two incisions 5,6 lying one behind the other (see FIG. 3), it has been found suitable to offset the incisions in neighbouring rows. This particular arrangement of the knives 3 has the effect that at the swelling of the injured body portion, this applies especially to bites on fingers and hands, the longitudinal buts 5, 6 open in the form of an ellipse, whereafter a small quantity of blood, but also mostly tissue liquor bringing out more poison than the blood itself, will be discharged.

The knives 3 are sharpened on both sides for forming rectilinear cutting edges 7 which run at right angles to the direction of penetration.

Rectilinear cutting edges 7 extending at right angles to the direction of penetration are of advantage for the reason that even when the knives penetrate to different depths, the length of the produced cuts 5,6 always remain the same and the danger of injuring a bone is eliminated.

The length of the knives 3 is preferably 4 mm and the distance a of two neighbouring rows of knives corresponds to half a knife length l. The knives 3 of two neighbouring rows of knives are offset by one knife length l. The height h of the knives 3 is 5 mm.

It can also be seen that the knife head 2 is connected to a spindle 8. The spindle 8 is provided with pin 10 which has a guide groove 9. In order to ensure the rotatable connection of the spindle 8 with the knife head 2, a setscrew 11 screwed into the knife head engages with its point the guide groove 9.

The spindle 8 is in engagement by its thread 12 with a path limiting member 13 which is movable in relation to the housing or holding part 1 in the interior thereof in the shifting direction of the knife head 2 but guided so as to be non-rotatable. Moreover, there is arranged in the interior housing a fixed stop 14 which limits the movement of the path limiting member 13 in the direction of percussion, thus to the right in FIG. 1. Between the path limiting member 13 and the cover 15 of the housing 1 is arranged a relatively strong compression spring 16 which is so strong that it is just possible to tension it.

In the path limiting member 13 is arranged a radially shiftable lock or snap-in sleeve 18 which is under the pressure of a compression spring 17. When the spindle 8 is moved backwards by pulling it with the aid of the knurled knob 19, the snap-in sleeve 18 will engage the bore 20 arranged in the housing wall, so that the device will then be in the tensioned condition ready for use. The release knob 21 serves for releasing the device. If the snap-in sleeve 18 is in the locking position, pressure on the release knob 21 will bring the snap-in sleeve 18 out of engagement with the bore 20, so that the knife head 3 is pushed out under the action of the compression spring 16.

The depth of the perforations produced by the knives 3 can be steplessly adjusted by a corresponding rotation of the spindle 8. As the front 22 of the housing 1 is applied to the tissue portion to be perforated when the device has to be used, the distance s by which the knives 3 project with their cutting edge 7 from this front 22 corresponds to the resulting depth of the perforations.

When the device is not used and is in the untensioned condition, the knife head 2 is withdrawn into the interior of the housing 1 by a corresponding rotation of the spindle 2 until the knives 3, too, are completely in the interior of the housing 1 and cannot be damaged.

In order to disinfect the knife head 2, one shifts it entirely out of the housing 1 by a corresponding rotation of the spindle 8, whereafter the knife head 2 can be detached from the spindle 8 after loosening the setscrew 11.

The treatment of an injury caused by a bite or sting of a poisonous animal proceeds as follows:

First of all a ligature is applied between the injury and the heart. The ligature should be made so tight that the lymphatic and venous blood streams to the respective portion of the body is stopped (the colour of the injured portion will become blue) but that the arterial connection is not impaired.

Then, according to the injured portion (for instance thicker fatty tissue or finger), the penetration depth s (FIG. 1) is so adjusted that cuts as deep as possible can be produced without injuring any bones.

Then the point of the bite or sting is disinfected with a disinfectant and the tissue perforating device is tensioned by a pull exerted on the spindle 8 until the snap-in sleeve 18 snaps in. Then one applies the front 22 of the housing 1 strongly to the injured portion so that the knives 3 extend parallel to the longitudinal direction of the limb concerned or parallel to any tendons, respectively, so that these are not severed but at the most cut in their longitudinal direction.

When the release knob 21 is pressed, the knife head 2 is pushed forward i.e. the knives 3 penetrate into the tissue concerned. Depending upon the position of the bite or sting, it may be necessary to perforate the tissue in a larger zone around the point concerned. By pressing the housing front 22 against the tissue, one obtains on the latter a pressure mark, so that one sees exactly where the front 22 of the housing 1 has to be positioned for the next shot so as to obtain a uniform perforation pattern.

The knives 3 penetrate through the epidermis into the subcutaneous tissue whereby mostly lymphatic gas and only to a slighter extend also subcutaneous blood vessels are opened.

The reticular skin (FIG. 3) produced in this manner prevents a taut swelling of the portion concerned whereby the danger of a pressure necrosis on tissues and nerves is reduced. Thus the usual extremely strong pain after a bite is avoided as well as the danger of a late necrosis.

After the perforation of the tissue portion concerned, a vacuum bell 24 connected to a vacuum device 23 is placed on the perforated bite portion and poison-containing tissue liquor is sucked off by means of the vacuum.

The vacuum device 23 functions in the following manner: At first the piston 25 is pushed forward against the action of the compression spring 27 by exerting with the thumb pressure on the push-rod 26, then the suction bell 24 is placed on the perforated tissue portion concerned so as to provide an air-tight seal and then the pressure of the thumb is released. Thus the compression spring 27 presses the piston 25 outward in the cylinder so that a vacuum is produced in the vacuum bell 24, which is connected with the interior of the cylinder 28.

It is suitable to apply at the same time circulation therapy, for instance with Cortisone (Registered Trade Mark).

I claim:

1. A tissue perforating device, for use in the treatment of body injuries of a person resulting from bites or stings of poisonous animals, comprising in combination, an elongated hollow holding member, a knife head normally disposed inside said holding member and being movable in opposite directions along said holding member, and operable to be rapidly advanced in one of said directions to project out of said holding member and adapted to move towards said body, and including at least two knives arranged side by side in with other knives off-set in relation to them, all the knives being substantially parallel to each other, a compression spring, a tensioning arrangement for placing the knife head under tension against the action of said spring thereby keeping it in the tensioned condition and a releasing arrangement operative for releasing the tensioned knife head so that it is abruptly moved in said one direction under the action of the compression spring, the cutting edge of each knife being substantially rectilinear and substantially perpendicular to said one direction whereby, when said knife head is rapidly moved in said one direction, the knives will penetrate the tissue of the body and make therein a plurality of substantially parallel incisions.

2. Device according to claim 1, further comprising a spindle rotatable relative to the knife head and longitudinally extending in the opposite direction beyond said holding member, said tensioning arrangement including a path limiting member movable relative to said holding member in said directions but guided so as to be non-rotatable, said spindle engaging said path limiting member, said holding member being provided with a stop which limits the movement of the path limiting member in said one direction.

* * * * *